United States Patent
Anderer

(10) Patent No.: US 9,833,754 B2
(45) Date of Patent: Dec. 5, 2017

(54) SAMPLE DILUTION TO SPECIFIABLE DILUTION RATIO

(71) Applicant: AGILENT TECHNOLOGIES, INC., Loveland, CO (US)

(72) Inventor: Herbert Anderer, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 294 days.

(21) Appl. No.: 14/443,126

(22) PCT Filed: Nov. 15, 2012

(86) PCT No.: PCT/IB2012/056461
§ 371 (c)(1),
(2) Date: May 15, 2015

(87) PCT Pub. No.: WO2014/076521
PCT Pub. Date: May 22, 2014

(65) Prior Publication Data
US 2015/0316455 A1    Nov. 5, 2015

(51) Int. Cl.
| | | |
|---|---|---|
| *B01F 3/08* | (2006.01) | |
| *B01F 15/02* | (2006.01) | |
| *B01F 15/00* | (2006.01) | |
| *G01N 35/10* | (2006.01) | |
| *G01N 30/06* | (2006.01) | |
| *G01N 1/38* | (2006.01) | |

(52) U.S. Cl.
CPC ............ *B01F 3/0865* (2013.01); *B01F 3/088* (2013.01); *B01F 15/00188* (2013.01);
(Continued)

(58) Field of Classification Search
CPC ................. B01F 3/0865; B01F 15/026; B01F 15/00422; B01F 15/00253;
(Continued)

(56) References Cited

U.S. PATENT DOCUMENTS

| | | |
|---|---|---|
| 4,186,607 A | 2/1980 | Porter et al. |
| 4,244,919 A | 1/1981 | Chen |
| (Continued) | | |

FOREIGN PATENT DOCUMENTS

| | | |
|---|---|---|
| CN | 1675529 A | 9/2005 |
| EP | 0305210 | 3/1989 |
| (Continued) | | |

OTHER PUBLICATIONS

Chinese Office action dated May 5, 2016 from related Chinese Application No. 201280077090.3.
(Continued)

*Primary Examiner* — Francis Gray

(57) ABSTRACT

A dilution apparatus (100) for diluting a fluidic sample in accordance with a specifiable dilution ratio, wherein the dilution apparatus (100) comprises a dilution fluid supply device (102) configured for supplying a dilution fluid at a first quantity per time, a transport fluid supply device (104) configured for supplying a transport fluid at a second quantity per time, a first fluid accommodation unit (106) configured for accommodating a first fluid volume, a second fluid accommodation unit (108) configured for accommodating a second fluid volume, and a control device (110, 112) configured for controlling the flow of the dilution fluid, the transport fluid and the fluidic sample so that in a first operation mode, the fluidic sample, being accommodated in the first fluid accommodation unit (106), is forced to flow to the second fluid accommodation unit (108) while being diluted by being mixed with dilution fluid, and in a second operation mode, the mixture of dilution fluid and fluidic sample, being accommodated in the second fluid accommodation unit (108), is forced to flow from the second fluid accommodation unit (108) to the first fluid accommodation unit (106) while being further diluted by being mixed with further dilution fluid.

27 Claims, 2 Drawing Sheets

(52) U.S. Cl.
CPC .. *B01F 15/00253* (2013.01); *B01F 15/00422* (2013.01); *B01F 15/026* (2013.01); *G01N 1/38* (2013.01); *G01N 30/06* (2013.01); *G01N 35/1097* (2013.01); *B01F 2003/0896* (2013.01); *B01F 2215/0037* (2013.01); *G01N 2001/383* (2013.01)

(58) Field of Classification Search
CPC ............... B01F 15/00188; B01F 3/088; B01F 2215/0037; B01F 2003/0896; G01N 1/38; G01N 30/06; G01N 35/1097; G01N 2001/383; G01N 24/00
See application file for complete search history.

(56) References Cited

U.S. PATENT DOCUMENTS

| | | | |
|---|---|---|---|
| 5,246,026 A | | 9/1993 | Proudman |
| 2004/0249105 A1* | 12/2004 | Nolte | ...................... B01F 3/088 528/44 |
| 2006/0128028 A1* | 6/2006 | Anderson | .............. G01N 30/24 436/173 |
| 2012/0285558 A1* | 11/2012 | Witt | ........................ F04B 13/00 137/544 |
| 2012/0305464 A1* | 12/2012 | Cormier | ................. G01N 30/20 210/198.2 |
| 2012/0314528 A1* | 12/2012 | Roth | ................... B01F 13/0059 366/160.5 |
| 2016/0077060 A1* | 3/2016 | Cormier | ............... G01N 1/2035 73/864.34 |

FOREIGN PATENT DOCUMENTS

| | | |
|---|---|---|
| JP | 2011-007666 A | 1/2011 |
| JP | 2011-13045 | 1/2011 |
| WO | WO99/45364 | 9/1999 |
| WO | WO2009/111229 | 9/2009 |
| WO | WO2010/099005 | 9/2010 |
| WO | WO2011/106162 | 9/2011 |

OTHER PUBLICATIONS

Machine translation of JP2011-13045.
International Search Report and Written Opinion dated Sep. 13, 2013 for International Application No. PCT/IB2012/056461.

* cited by examiner

SAMPLE DILUTION TO SPECIFIABLE DILUTION RATIO

The present application is a National Stage Application under 35 U.S.C. §371 and claims priority under 35 U.S.C. §121 from international Patent Application No. PCT/IB2012/056461 filed on Nov. 15, 2012. The entire disclosure of International Patent Application No. PCT/IB2012/056461 is specifically incorporated herein by reference.

BACKGROUND ART

The present invention relates to a dilution apparatus, a process monitoring apparatus, a method of diluting a fluidic sample, and a software program or product.

For various applications, for instance in analytical chemistry, it is necessary to experimentally investigate a fluidic sample. However, it may happen that a detector has only a limited range of intensities within which it can deliver meaningful output results. If a fluidic sample is highly concentrated exceeding the requirements of a detector, an overflow of the detector may occur so that the output result of the detector is not usable. For this and other purposes, it may be required to dilute a fluidic sample, for instance to reduce its concentration to a value which can be handled by a detector.

However, in order to be able to interpret a detector signal correctly, it may be further desired to know which dilution ratio has been applied to the fluidic sample, i.e. which amount of a fluidic sample (in terms of volume or mass) corresponds to which amount of diluting fluid (in terms of volume or mass) with which the fluidic sample has been mixed for dilution. Diluting fluid is a fluid used for diluting the fluidic sample, i.e. being particularly free of components of the fluidic sample generating a detector signal or, more generally, being the fluid under analysis.

Conventionally, fluid dilution may be performed as disclosed by WO 1999/45364, WO 2009/111229, JP 2011-13045, WO 2010/099005, U.S. Pat. No. 4,244,919, or WO 2011/106162.

It is still difficult to dilute a fluidic sample by diluting fluid with a dilution rate being precisely definable over a broad range and being simple in operation.

DISCLOSURE

It is an object of the invention to provide a simply operable system which allows to dilute a fluidic sample with diluting fluid with a dilution rate being precisely definable over a broad range. The object is solved by the independent claims. Further embodiments are shown by the dependent claims.

According to an exemplary embodiment of the present invention, a dilution apparatus for diluting a (particularly predefined quantity of) fluidic sample (such as a liquid and/or gaseous medium, optionally including also solid particles, which is to be analyzed and which may comprise a plurality of fractions of molecules or particles which shall be separated)—particularly in accordance with a specifiable dilution ratio, i.e. ratio between volume or mass of fluidic sample and volume or mass of dilution fluid)—is provided, wherein the dilution apparatus comprises a dilution fluid supply device (particularly a dilution fluid reservoir having a conveying or pumping unit for conveying or pumping dilution fluid) configured for supplying a dilution fluid at a (particularly predefined) first quantity per time (particularly at a first flow rate, i.e. fluid volume per time or fluid mass per time), a transport fluid supply device (particularly a transport fluid reservoir having a conveying or pumping unit for conveying or pumping transport fluid) configured for supplying a transport fluid at a (particularly predefined) second quantity per time (particularly at a second flow rate, i.e. fluid volume per time or fluid mass per time), a first fluid accommodation unit (particularly a first fluid loop or buffer volume having a predefined first capacity of accommodating fluid) configured for accommodating a (particularly predefined) first fluid volume, a second fluid accommodation unit (particularly a second fluid loop or buffer volume having a predefined second capacity of accommodating fluid) configured for accommodating a (particularly predefined) second fluid volume, and a control device configured for controlling flow conditions of the dilution fluid, the transport fluid and the fluidic sample so that in a first operation mode, the fluidic sample, being accommodated in the first fluid accommodation unit, is forced to flow to the second fluid accommodation unit while being diluted by being mixed with (particularly a predefined quantity of) dilution fluid (but preferably not with transport fluid), and in a (subsequent) second operation mode, the mixture of dilution fluid and fluidic sample, being accommodated in the second fluid accommodation unit, is forced to flow back from the second fluid accommodation unit back to the first fluid accommodation unit while being further diluted by being mixed with (particularly a predefined quantity of) further dilution fluid (but preferably not with transport fluid).

According to another exemplary embodiment of the present invention, a process monitoring apparatus for monitoring a process of processing processing fluid is provided, wherein the process monitoring apparatus comprises a fluidic sample supply device configured for supplying a (particularly predefined quantity of) fluidic sample from the processing fluid, a dilution apparatus having the above-mentioned features and configured for being supplied with the fluidic sample and for diluting the supplied fluidic sample (particularly in accordance with a specifiable dilution ratio), a diluted fluidic sample drain device configured for draining (particularly a predefined quantity of) diluted fluidic sample, and an analysis device configured for analyzing the drained diluted fluidic sample for monitoring the process.

According to another exemplary embodiment of the present invention, a method of diluting a fluidic sample (particularly in accordance with a specifiable dilution ratio) is provided, wherein the method comprises supplying a dilution fluid at a first quantity per time, supplying a transport fluid at a second quantity per time, supplying the fluidic sample (particularly a predefined amount, more particularly a predefined volume or a predefined mass, of fluidic sample), and controlling the flow of the dilution fluid, the transport fluid and the fluidic sample so that in a first operation mode, the fluidic sample, being accommodated in a first fluid accommodation unit configured for accommodating a first fluid volume, is forced to flow to a second fluid accommodation unit configured for accommodating a second fluid volume while being diluted by being mixed with dilution fluid, and in a second operation mode, the mixture of dilution fluid and fluidic sample, being accommodated in the second fluid accommodation unit, is forced to flow from the second fluid accommodation unit to the first fluid accommodation unit while being further diluted by being mixed with further dilution fluid.

According to still another exemplary embodiment of the present invention, a software program or product is provided, preferably stored on a data carrier, for controlling or executing the method having the above mentioned features, when run on a data processing system such as a computer.

Embodiments of the invention can be partly or entirely embodied or supported by one or more suitable software programs, which can be stored on or otherwise provided by any kind of data carrier, and which might be executed in or by any suitable data processing device. Software programs or routines can be preferably applied in the context of fluid dilution control. The fluid dilution control scheme according to an embodiment of the invention can be performed or assisted by a computer program, i.e. by software, or by using one or more special electronic optimization circuits, i.e. in hardware, or in hybrid form, i.e. by means of software components and hardware components.

According to an exemplary embodiment of the invention, a mixing of a fluidic sample with dilution fluid is performed in a very precise way by providing a source of dilution fluid at a dilution fluid interface of a fluidic network (i.e. a bifurcated arrangement of interconnected fluidic conduits). The dilution fluid may be provided with an adjustable first quantity per time, particularly flow rate, and a transport fluid (supplied at a transport fluid interface of the fluidic network) may be supplied with an adjustable second quantity per time, for instance flow rate. The transport fluid does preferably not mix with the sample or mixture but pushes it with a defined flow rate towards a mixing position at which mixing between the sample or mixture and dilution fluid occurs. By alternatingly switching between two operation modes of the dilution system, the relative ratio between the two quantities per time will have a deterministic impact on the dilution ratio of the fluidic sample which is supplied to the fluidic network and mixed with the dilution fluid. At the beginning of the procedure, the fluidic sample is conveyed to or supplied at a first accommodation volume which is a pre-known buffer volume capable of storing the fluidic sample to be diluted. Then, the fluidic sample is driven, particularly by a fluid drive in combination with a correspondingly switched fluidic valve, towards a second fluid accommodation unit. As the first fluid accommodation unit, also the second fluid accommodation unit is a well-defined buffer volume. The second fluid accommodation unit is capable of storing the fluidic sample already diluted by dilution fluid, as will be explained in the following. When, in the first operation mode, the fluidic sample is driven from the first fluid accommodation unit to the second fluid accommodation unit, it starts flowing to the second fluid accommodation unit under the influence of the transport fluid flowing in the same direction. For instance at a fluidic bifurcation of the fluidic network, the fluidic sample is then mixed with dilution fluid. Such a bifurcation may be a T-piece or other kind of flow combiner combining the fluidic sample with the dilution fluid. This mixture of these fluids then arrives at the second fluid accommodation unit and is stored there temporarily. In view of the known quantities per time of the dilution fluid and the transport fluid as well as in view of the quantity of fluidic sample, the dilution ratio of the fluidic sample at the position of the second fluid accommodation unit, i.e. after a first dilution stage, is therefore determinable. Now, a second operation mode of the dilution system can be activated, for instance by correspondingly switching a fluidic valve (or valves) for changing (particularly inverting) the flow direction of the mixture of the fluidic sample and the dilution fluid. As a result of this switching, the mixture of the fluidic sample and the dilution fluid flows back towards the first fluid accommodation unit, again driven by the transport fluid. At the flow combiner, the mixture of the already diluted fluidic sample is then mixed with further dilution fluid until the resulting mixture reaches again the first fluid accommodation unit, i.e. after a second dilution stage. In view of the well-defined first quantity per time and second quantity per time, the fluidic sample has now been further diluted to a second well-defined dilution ratio. By optionally repeating this switching procedure between the first and the second operation mode, the fluidic sample undergoes a reciprocating flowing motion between the first and second fluid accommodation units, thereby oscillating and being successively diluted in each stage in a predictable way.

By branching off a defined amount of fluidic sample—as a sample of processing fluid to be processed in terms of a certain application—and by analysing the fluidic sample after the mentioned dilution, simple and efficient process monitoring may be performed. Particularly, the dilution may be performed so as to adjust the concentration of the diluted sample to needs of a detector in the analysis path.

In the following, further exemplary embodiments of the dilution apparatus, the process monitoring apparatus, the method, and the software program or product will be explained.

The skilled person will understand that it is also possible to implement more than two fluid accommodation units and/or more than two dilution fluid supply units and/or more than two operation modes to further refine the predictable fluidic sample dilution procedure. It is for instance also possible to use one common dilution fluid container as a source for both the dilution fluid and the transport fluid and/or one common pump for pumping dilution fluid and the transport fluid.

In an embodiment, the control device is configured for adjusting the quantity per time of supplying the dilution fluid and/or the quantity per time of supplying the transport fluid to thereby adjust the dilution ratio to a specifiable, particularly to a user-defined or a predefined, dilution ratio. For instance, a user or an apparatus may supply a control command to the dilution system instructing the latter to dilute the sample to a desired dilution ratio, for instance 1:1000. When the ratio between the mixing volumes of the dilution fluid and the transport fluid is for instance selected to be 9:1, each motion of the fluidic sample from one of the fluid accommodation units to the other one will result in a further dilution of a factor 10, wherein only a part of the respective mixture is usually used for the next dilution stage. Thus, it is possible to use the first quantity per time and the second quantity per time as control parameters for adjusting a certain dilution ratio. The first quantity per time and the second quantity per time may, in one embodiment, be the same, resulting in a reduction of the concentration of the fluidic sample by factor of two upon each switch between the operation modes. The first quantity per time and the second quantity per time may however also be different, thereby allowing to adjust significantly higher dilution ratios with great precision.

In an embodiment, the control device is configured for alternatingly changing or switching between the first operation mode and the second operation mode a specifiable number of times to thereby adjust the dilution ratio to a specifiable dilution ratio. Hence, as another control parameter for adjusting a certain dilution ratio, the number of switches between the operation modes can be used by the system to obtain a user-defined or machine-controlled dilution ratio of the fluidic sample. In other words, if a dilution ratio per switch between operation modes is defined by the first quantity per time and the second quantity per time, this one stage dilution ratio can be multiplied n times if n is the number of switches between the two operation modes. Thus, even extremely high dilution ratios may be obtained by simply repeating the simple switching logic as described above. For instance, when the ratio between the mixing volumes of the dilution fluid and the transport fluid is for instance 9:1, and the number of dilution stages (i.e. switches between the first and the second operation mode) is three, the dilution ratio will be 10·10·10=1000.

Therefore, by adjusting the ratio between the quantities per time of the dilution fluid and the transport fluid in combination with a selection of a number of times according to which the fluidic sample oscillates between the first fluid accommodation unit and the second fluid accommodation unit, a precisely specifiable dilution ratio may be obtained with a very simple fluidic system. Moreover, an extremely small dilution ratio may be adjusted in short time and with high precision.

In an embodiment, the dilution fluid supply device and the transport fluid supply device are configured for supplying the same kind of fluid (particularly the same chemical) as dilution fluid and as transport fluid. For instance, both fluid supply devices may supply a liquid solvent as the respective dilution fluid. For example, both fluid supply devices may deliver water or an organic solvent (such as acetonitrile or methanol) as dilution fluid. When using the same fluid for both the dilution fluid supply device and the transport fluid supply device, even the same fluid source may be shared between the two fluid supply devices. However, by allowing alternatively both fluid supply devices to use difficult types of dilution fluid, the fluids may be specifically selected to properly fulfill the respective tasks of diluting (and mixing) on the one hand and transporting (but not mixing) on the other hand.

In an embodiment, the control device comprises a fluidic control valve being switchable to operate the dilution apparatus between the first operation mode and the second operation mode. In the context of this application, the term "fluidic valve" may particularly denote a fluidic component which has fluidic interfaces, wherein upon switching the fluidic valve selective ones of the fluidic interfaces may be selectively coupled to one another so as to allow fluid to flow along a corresponding fluidic path, or may be decoupled from one another, thereby disabling fluid communication. A fluidic valve can be considered as a fluidic member which allows to enable or disable different fluid flow paths, thereby allowing to switch between the first and the second operation mode by simply operating the fluidic valve alternatingly in a forward and in a backward direction which allows for a very simple operation.

In an embodiment, the control device is configured for switching the fluidic control valve to move the fluidic sample alternatingly along a first direction in the first operation mode and along a second direction in the second operation mode, the second direction being opposite or inverse to the first direction. Simply alternating between a forward flow mode and a backward flow mode of the mixture allows to perform the dilution in a very small fluidic network, because the same fluidic channels can be used for the various dilution stages. Particularly, the flow of the fluids may occur in an annular (such as a circular) conduit, particularly alternatingly in a counterclockwise or in a clockwise direction.

In an embodiment, the fluidic control valve comprises a first valve member (particularly a stator) comprising ports and a second valve member (particularly a rotor) comprising grooves configured for fluidically coupling selectable ones of the ports depending on a relative orientation between the first valve member and the second valve member which are movable (particularly rotatable) relative to one another. Particularly, the adjustment of the relative orientation between the first fluidic member and the second fluidic member may be made by a relative rotation between these fluidic members. Hence, one of the valve members may be a rotor and another one may be a stator. The ports forming fluid connections to the various components of the fluidic network can for instance be provided at the stator, whereas the grooves closing fluidic connections between definable ones of the ports can be provided at the rotor. However, in an alternative embodiment, it is also possible to use a fluidic valve with valve members being movable relative to one another in a translatory way.

In an embodiment, a first port is fluidically coupled to the first fluid accommodation unit, a second port is fluidically coupled to the second fluid accommodation unit, a third port is fluidically coupled to the transport fluid supply device, and a fourth port is fluidically coupled to a waste line, wherein the dilution fluid supply device is fluidically connected between the first fluid accommodation unit and the second fluid accommodation unit, and wherein the fluidic valve is switchable so that in the first operation mode, one groove connects the first port to the third port and another groove connects the second port with the fourth port in the second operation mode, one of the grooves connects the first port to the fourth port and the other one of the grooves connects the second port with the third port. Thus, a very simple four-ports-two-groove fluidic control valve may be used for supporting the desired switches between the operation modes. By taking this measure, a very compact dilution system can be obtained. With such a configuration, the switching between the two operation modes may be performed in a very simple way by simply alternating switching the fluidic control valve forwardly and backwardly. However, it should be said that other valve configurations are possible as well.

In an embodiment, the control device may be configured for, prior to each switch between the first operation mode and the second operation mode, draining a portion of the mixture (of fluidic sample and dilution fluid) towards a waste line until the entire fluid volume of the respective one of the fluid accommodation units (the one which is presently the target to which the sample or mixture is presently transported) is completely filled with the mixture before further diluting the remaining portion of the mixture after a subsequent change of the operation mode. For instance, the partial volume of the mixture used for the subsequent dilution stage may always remain constant and may be identical to the fluid volume or capacity of the respective fluid volume. By draining a controllable part of the present mixture into a waste container, the adjustment of the dilution ratio can be performed very accurately since it can be ensured that the next dilution stage starts only with a mixture having a defined composition or sample concentration.

In an embodiment, the transport fluid supply device is configured, in each of the first and the second operation mode, for pressing the transport fluid towards a back end of the fluidic sample or the mixture to thereby drive the fluidic sample or the mixture to a position at which mixing or further mixing with dilution fluid occurs. Therefore, the transport fluid simply provides a force to move the sample or present mixture to a position at which further mixing occurs. The flow rate of the transport fluid defines the flow rate of the sample or present mixture, and has therefore a predictable impact on the dilution ratio.

In an embodiment, the transport fluid supply device is configured, in each of the first and the second operation mode, for pressing the transport fluid towards a back end of the fluidic sample or the mixture without mixing the fluidic sample or the mixture with transport fluid so that the mixture (between sample and diluent) always remains free of transport fluid. Hence, the transport fluid fulfills only a sample transport task and serves for driving the sample or present mixture with a defined flow rate, but does not become part of the mixture between sample and dilution fluid, which mixture is further diluted in subsequent stages.

In an embodiment, the dilution apparatus comprises a mixing point, particularly a flow combiner (such as a fluidic T-piece or Y-piece), fluidically connecting a flow path from the first fluid accommodation unit, a flow path from the second fluid accommodation unit and a flow path from the dilution fluid supply device to enable mixing between the fluidic sample or the mixture with dilution fluid. At this mixing point connecting three fluid lines, mixing between dilution fluid and sample or present mixture takes place in each mixing stage.

In an embodiment, the mixing point is an active mixer or a passive mixer. A passive mixer results in mixing only by bringing together fluids to be mixed at the mixing point. Turbulent flow and discontinuities at such a mixing point then result in the mixing. In case of an active mixer, an active provision of promoting mixing is taken, such as providing one or more rotating blades, a turbulence promoter, etc.

In an embodiment, the analysis device comprises a sample separation device configured for separating different fractions of the diluted fluidic sample. In the context of this application, the term "sample separation device" may particularly denote any apparatus which is capable of separating different fractions of a diluted fluidic sample by applying a certain separation technique. A separation device may particularly denote a fluidic member through which the diluted fluidic sample is transferred and which is configured so that, upon conducting the diluted fluidic sample through the separation device, the fluidic sample will be separated into different groups of molecules or particles (called fractions). An example for a separation device is a liquid chromatography column which is capable of trapping or retarding and selectively releasing different fractions of the fluidic sample. Thus, after having diluted the fluidic sample to a predefinable dilution ratio, at least a part of the diluted fluidic sample may be branched off to the analysis unit which can then perform a separation of the diluted fluidic sample into its various fractions (a remaining part of the diluted fluidic sample may be conveyed to a waste line). Thus, the absolute and/or relative concentrations of fractions of the diluted fluidic sample may be used for monitoring also the process in which a concentrated fluidic sample, i.e. having properties of the processing fluid, is processed. For example, if a technical problem occurs in a processing path of manufacturing a pharmaceutical component, this can be rapidly detected by the analysis unit so that a corresponding feedback signal for regulating or stopping the processing path can be supplied. By taking this measure, any problem in the processing path may be detected basically in real-time so that corresponding counter-measures may be taken rapidly to overcome this technical problem. Alternatively, the processing path may also be deactivated until the problem is solved.

In an embodiment, the sample separation device is a liquid chromatography device configured for separating different fractions of the diluted fluidic sample by liquid chromatography. The sample separation may be performed by liquid chromatography, or alternatively by gas chromatography. A liquid chromatography system is particularly suitable for analyzing a branched off dilution fluid sample, since the output of the dilution system is very similar to what is provided by an injector of a liquid chromatography device.

In an embodiment, the liquid chromatography device comprises a fluid drive configured to drive a mobile phase and the diluted fluidic sample along a separation path, and a chromatographic column located in the separation path downstream of the fluid drive and being configured for separating the fractions of the diluted fluidic sample fluid in the mobile phase. In the context of this application, the term "fluid drive" may particularly denote any kind of pump which is configured for conducting a mobile phase and/or a diluted fluidic sample along a fluidic path. In the context of this application, the term "downstream" may particularly denote that a fluidic member located downstream compared to another fluidic member will only be brought in interaction with the diluted fluidic sample after interaction with the other fluidic member (hence being arranged upstream). Therefore, the terms "downstream" and "upstream" relate to a flowing direction of the diluted fluidic sample. The terms "downstream" and "upstream" may also relate to a preferred direction of the fluid flow between the two members being in downstream-upstream relation. Therefore, the diluted fluidic sample, which may be at a relatively low pressure (for instance at or close to the atmospheric pressure) may be switched using a suitable further fluidic drain valve into a chromatographic separation path between a fluid drive such as a high pressure pump (for instance operating in a pressure range between 20 bar and 2000 bar) and a chromatographic column having an adsorption material capable of adsorbing fractions of the fluidic sample. After adsorption, desorption of the individual fractions of the fluidic sample may then be triggered by for instance by modifying a solvent composition, known to a skilled person as a gradient run.

In an embodiment, the liquid chromatography device comprises a sample injector configured to receive the diluted fluidic sample from the diluted fluidic sample drain device and to guide the diluted fluidic sample into the mobile phase. For instance, the second fluid accommodation unit of the dilution system may be used as a sample loop of an injector of a liquid chromatography apparatus.

In an embodiment, the liquid chromatography device comprises a degassing apparatus for degassing the mobile phase. By using a degassing apparatus for degassing a mobile phase before mixture with the diluted fluidic sample, the chromatographic separation performance may be significantly improved.

In an embodiment, the analysis device comprises a detector configured to detect separated fractions of the diluted fluidic sample. For example, such a detector may be a flow cell having a fluorescence detector or the like.

In an embodiment, the analysis device comprises a collection device configured to collect separated fractions of the diluted fluidic sample. Thus, the separated components of the diluted fluidic sample may even be stored in separate containers, for example for documentation purposes.

In an embodiment, the analysis device is configured to analyze at least one physical, chemical and/or biological parameter of at least one compound of the diluted fluidic sample. The monitoring of such a parameter may also allow to indirectly monitor the processing path.

In an embodiment, the analysis device comprises at least one of the group consisting of a chromatography device, a liquid chromatography device, an HPLC device, a gas chromatography device, a capillary electrochromatography device, an electrophoresis device, a capillary electrophoresis device, a gel electrophoresis device, and a mass spectroscopy device. However, many other kinds of analysis devices may be used as well.

In an embodiment, the sample separation device may be configured for performing a separation in accordance with liquid chromatography, supercritical-fluid chromatography, capillary electrochromatography, electrophoresis and gas chromatography. However, alternative separating technologies may be applied as well.

The sample separation device may be filled with a separating material. Such a separating material which may also be denoted as a stationary phase may be any material which allows an different degree of interaction with sample components so as to be capable of separating different components of such a sample. The separating material may be a liquid chromatography column filling material or packing material comprising at least one of the group consisting of polystyrene, zeolite, polyvinylalcohol, polytetrafluoroethylene, glass, polymeric powder, carbon, graphite, alumina, zirkonia, silicon dioxide, and silica gel, or any of above with chemically modified (coated, capped etc) surface. However, any packing material can be used which has material properties allowing a sample passing through this material to be separated into different components, for instance due to different degrees of interactions or affinities between the packing material and fractions of the analyte. In still another embodiment a sample separation device, particularly a second sample separation device, may be a so called open tubular column, i.e. a channel without filling material but with walls capable of selective interaction with sample components.

At least a part of the separation device may be filled with a separating material, wherein the separating material may comprise beads having a size in the range of essentially 0.1 μm to essentially 50 μm. Thus, these beads may be small particles which may be filled inside the separation section of the microfluidic device. The beads may have pores having a size in the range of essentially 0.005 μm to essentially 0.2 μm. The fluidic sample may enter the pores, wherein an interaction may occur between the fluidic sample and the surface of the pores.

The sample separation apparatus may be configured as a fluid separation system for separating components of the sample. When a mobile phase including a fluidic sample is passed through the fluidic device, for instance by applying a high pressure, the interaction between a filling of the column and the fluidic sample may allow for separating different components of the sample, as performed in a liquid chromatography device.

However, the sample separation apparatus may also be configured as a fluid purification system for purifying the fluidic sample. By spatially separating different fractions of the fluidic sample, a multi-component sample may be purified, for instance a protein solution. When a protein solution has been prepared in a biochemical lab, it may still comprise a plurality of components. If, for instance, only a single protein of this multi-component liquid is of interest, the sample may be forced to pass the columns. Due to the different interaction of the different protein fractions with the filling of the column, the different sample components may be distinguished, and one component or band of material may be selectively isolated as a purified sample.

The sample separation device may be a chromatographic column for separating components of the fluidic sample. Therefore, exemplary embodiments may be particularly implemented in the context of a liquid chromatography apparatus.

The sample separation apparatus may be configured to conduct the mobile phase through the system by means of a high pressure, particularly of at least 400 bar, more particularly of at least 1000 bar.

The sample separation apparatus or its parts or sub-devices may be configured as a microfluidic device. The term "microfluidic device" may particularly denote a fluidic device as described herein which allows to convey fluid through microchannels having a dimension in the order of magnitude of less than 500 μm, particularly less than 200 μm, more particularly less than 100 μm or less than 50 μm or less. The sample separation apparatus may also be configured as a nanofluidic device. The term "nanofluidic device" may particularly denote a fluidic device as described herein which allows to convey fluid through nanochannels having even smaller dimensions than the microchannels.

In an embodiment, the process monitoring apparatus comprises a fluid processing device configured for processing the processing fluid, wherein the fluidic sample supply device is configured for supplying the fluidic sample from the fluid processing device to the first fluid accommodation unit. Thus, three basic components may be foreseen in the process monitoring apparatus: Firstly, the fluid processing device which actually processes the processing fluid, for example to process a fluid for manufacture of a medication. Secondly, the dilution system for branching off or splitting off a fluidic sample from the fluid processing device and diluting the latter in a reproducible and well-defined way. Thirdly, the analysis device analyzing the diluted fluidic sample and being capable to do so in view of the reproducible dilution of the fluidic sample beforehand. By this dilution, the concentration of the diluted fluidic sample may be adjusted to correspond to a concentration range within which a detector in the analysis device functions properly. Therefore, a fully automated process monitoring device is provided which allows at any time to detect whether a property of the processing fluid leaves a predefined range of acceptable values.

In an embodiment, the fluid processing device comprises a product manufacturing device, a pharmaceutical process device, or an experimental process device. However, apart from these specific examples, exemplary embodiments of the invention may be implemented in many very different kinds of fluid processing devices as well.

In an embodiment, the fluidic sample supply device comprises a fluidic supply valve being switchable so as to transfer fluidic sample from the fluid processing device to the first fluid accommodation unit. Thus, the fluidic interface between the fluid processing device and the dilution device may be realized by a further fluidic valve. The latter may be switched between a first operation mode in which the fluid processing device is fluidically decoupled from the dilution system and works completely independently from the dilution device, and a second operation mode in which the fluidic sample is branched off the fluid processing device to monitor the fluid processing regularly or occasionally.

For instance, the processing fluid may flow along a fluidic path which includes two ports and an interconnecting groove of the further fluidic valve. Upon correspondingly switching this further fluidic valve, a predefined amount of processing fluid may be loaded onto the first fluid accommodation unit which may be connected between two further ports of the further fluidic valve. In other words, the first fluid accommodation unit may be switched between a first operation mode in which it is coupled to the fluid processing device and a second operation mode in which it is coupled to the fluid dilution system.

In an embodiment, the diluted fluidic sample drain device comprises a fluidic drain valve being switchable so as to transfer diluted fluidic sample from the second fluid accommodation unit to the analysis device. Thus, also the fluidic interface between the dilution device and the analysis device may be realized by a further fluidic valve. During diluting, the second fluid accommodation unit may be connected via ports of this further fluidic valve so as to form part of the dilution device. If however the diluted fluidic sample is to be supplied to the analysis device, this further fluidic valve is switched so that the second fluid accommodation unit forms part of the analysis path of the analysis device.

In an embodiment, the fluidic supply valve and/or the fluidic drain valve comprises a first valve member (particularly a stator) comprising ports and a second valve member (particularly a rotor) comprising grooves configured for fluidically coupling selectable ones of the ports depending on a relative orientation between the first valve member and the second valve member which are movable (particularly rotatable) relative to one another. Particularly, the adjustment of the relative orientation between the first fluidic member and the second fluidic member may be made by a relative rotation between these fluidic members. Hence, one of the valve members may be a rotor and another one may be a stator.

BRIEF DESCRIPTION OF DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

Figure 1:
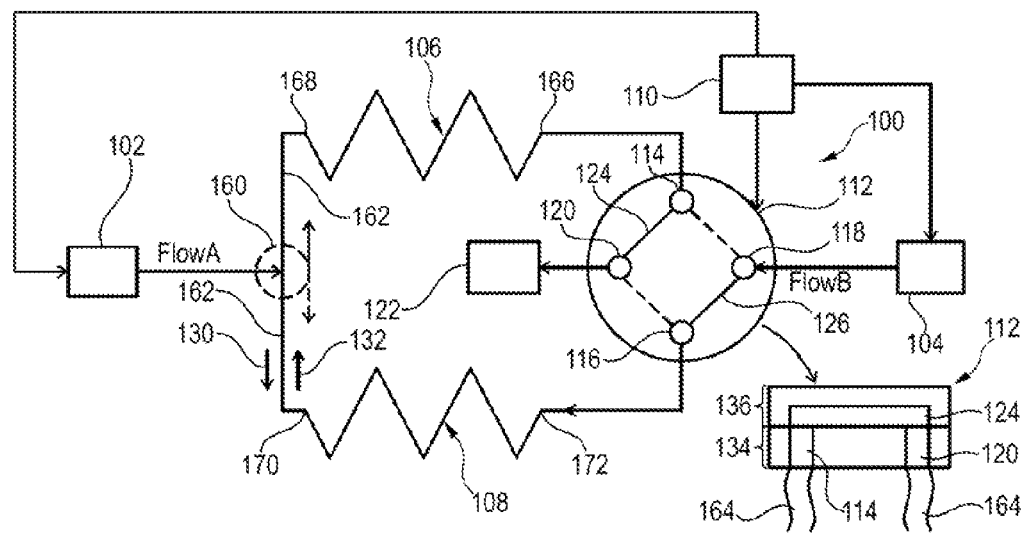
FIG. 1 shows the setup of a dilution apparatus for diluting a fluidic sample in accordance with a specified dilution ratio according to an exemplary embodiment of the invention.

The illustration in the drawing is schematic.

In the following, referring to FIG. 1, a dilution apparatus 100 for diluting a biological fluidic sample according to an exemplary embodiment of the invention will be explained. Operation of dilution apparatus 100 will be explained in accordance with the example of a user-specified dilution ratio of 1:1000.

The fluidic sample can be injected or loaded onto a first fluid accommodation unit 106 such as a fluid loop having a certain buffer volume of accommodating fluid. A predefined amount of the fluidic sample can be loaded onto this first fluid accommodation unit 106 serving as a buffer volume. The predefined amount of the fluidic sample shall be selected so that it completely fills at least the entire fluid volume of the first fluid accommodation unit 106. A dilution fluid supply unit 102 is connected at a flow combiner 160 of a fluidic network 162 and is configured for supplying a dilution fluid with an adjustable first flow rate. The fluidic network 162 consists of a number of fluidic channels which are interconnected in the way as shown in FIG. 1. Furthermore, a transport fluid supply device 104 is provided which is configured for supplying a transport fluid with an adjustable second flow rate. In the shown embodiment, the first flow rate according to which the dilution fluid supply device 102 delivers the dilution fluid is 900 µl/min. In contrast to this, the transport fluid supply device 104 delivers the transport fluid with a flow rate of 100 µl/min. In the shown embodiment, the dilution fluid and the transport fluid are both water.

As can be further taken from FIG. 1, a fluidic control valve 112 is interconnected within the fluidic network 162. More precisely, the fluidic control valve 112 comprises, as shown in a cross-sectional view in FIG. 1, a stator valve member 134 and a rotor valve member 136. The stator valve member 134 and the rotor valve member 136 are rotatable relative to one another so as to enable and disable certain flow paths in accordance with each rotation state. As can further be taken from the detail in FIG. 1, fluid connection lines 164 of the fluidic network 162 are connected to ports 114, 120 which are formed as through-holes in the stator valve member 134. Correspondingly, a fluidic groove 124 is formed in the rotor valve member 136. By rotating the rotor valve member 136 relative to the stator valve member 134, various fluidic paths between ports 114, 120 and other ports 116, 118 may be enabled or may be disabled by groove 124 and another groove 126.

Coming back to the main image of FIG. 1, a first port 114 of the fluidic control valve 112 is fluidically connected to a first interface 166 of the first fluid accommodation unit 106. A second fluidic interface 168 of the first fluid accommodation unit 106 is directly connected to the flow combiner 160. Furthermore, a first fluidic interface 170 of the second fluid accommodation unit 108 is connected to the flow combiner 160. A second fluidic interface 172 of the second fluid accommodation unit 108 is connected to second port 116 of the fluidic control valve 112. Third port 118 of the fluidic control valve 112 is connected to the transport fluid supply device 104. Furthermore, fourth port 120 of the fluidic control valve 112 is connected, via a waste line, to a waste container 122.

As can furthermore be taken from FIG. 1, the fluidic control valve 112 has first groove 124 and second groove 126 which, in a first operation mode (not shown in FIG. 1, but indicated with dashed lines), interconnect the first port 114 with the third port 118 and the second port 116 with the fourth port 120. In an alternative second operation mode (shown in FIG. 1, solid lines), one of the grooves 124, 126 connects the first port 114 with the fourth port 120 and the other of the grooves 126, 124 connects the second port 116 with the third port 118.

A controller 110 (such as a processor which may be software-controlled) controls switching of the fluidic control valve 112, supply of dilution fluid by the dilution fluid supply device 102 and supply of the transport fluid by the transport fluid supply device 104.

In the following, the two different operation modes of the dilution apparatus 100 will be explained. The controller 110 controls alternating switches between these two operation modes to perform a predefined dilution performance. In the first operation mode, the fluidic sample is firstly stored or buffered at the first fluid accommodation unit 106. The fluidic control valve 112 is switched to a configuration in which the transport fluid supply device 104 delivers transport fluid via third port 118, groove 124, first port 114 to the first fluid accommodation unit 106 so as to press the stored fluidic sample away from the first fluid accommodation unit 106 with a defined flow rate. Since the transport fluid presses the fluidic sample forwardly (i.e. to the left hand side of the first fluid accommodation unit 106 in FIG. 1) without being mixed with it, the fluidic sample will flow with a flow rate being equal or basically equal to the flow rate of the transport fluid. The fluidic sample is then combined and mixed, at the flow coupler 160, with dilution fluid supplied by the dilution fluid supply device 102. The mixture of the fluidic sample and the dilution fluid then flows along a flow direction 130 onto the second fluid accommodation unit 108. In view of the flow rates of the dilution fluid of 900 μl/min (Flow A) and of the transport fluid (and hence of the fluidic sample) of 100 μl/min (Flow B), the diluted sample arriving at the second fluid accommodation unit 108 has already been diluted to a dilution ratio of 1:10:

$$\text{Dilution Ratio} = \text{Flow}B : (\text{Flow}A + \text{Flow}B)$$

After this first dilution stage and in preparation of the subsequent second dilution stage, a part of the diluted fluidic sample may be drained in the waste container 122 via the fluidic control valve 112 to ensure that the whole fluid volume of the second fluid accommodation unit 108 is filled with fluidic sample being diluted with the dilution fluid with a spatially constant, reproducible, defined and predictable concentration—before a switch to a subsequent operation mode occurs.

Now, the fluidic control valve 112 is switched under control of the controller 110 so that further transport fluid is supplied from the transport fluid supply device 104 via third port 118, one of the grooves 124, 126 and the second port 116 to the second fluid accommodation unit 108 so that the already diluted fluidic sample, forced by the further transport fluid, is transported along an opposite flow direction 132 towards the flow coupler 160. Hence, the stored diluted fluidic sample flows away from the second fluid accommodation unit 108 with a defined flow rate. Since the transport fluid presses the diluted fluidic sample forwardly (i.e. to the left hand side of the first fluid accommodation unit 108 in FIG. 1) without being mixed with it, the diluted fluidic sample will flow with a flow rate being equal or basically equal to the flow rate of the further transport fluid. At the flow coupler 160, the diluted fluidic sample is mixed with further dilution fluid supplied from the dilution fluid supply unit 102. Therefore, an even stronger diluted mixture of the diluted fluidic sample and the further dilution fluid is accommodated in the first fluid accommodation unit 106. Now the dilution ratio is 1:100 (compare the above formula and the above values of the flow rates).

The described switching performance resulting in an oscillation of the dilution fluid between one of the fluid accommodation units 106, 108 and the other one can be initiated merely by switching the valve 102 forwardly and backwardly, so as to repeat the first operation mode and the second operation mode a predefined number of times.

Thus, by adjustment of the first flow rate, the second flow rate and the number of switching procedures, the dilution rate can be adjusted.

Figure 3:
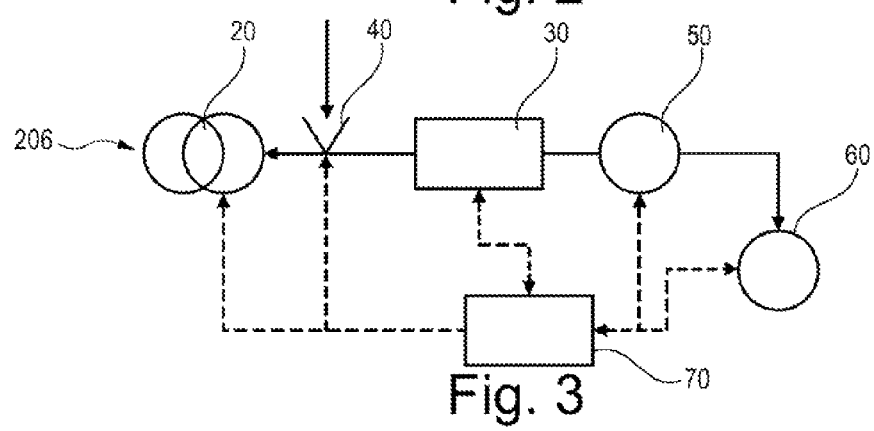
FIG. 3 illustrates a liquid chromatography system as an example for an analysis system for analyzing a diluted fluidic sample according to an exemplary embodiment.

In an alternative embodiment, the waste container 122 may be substituted by a further fluid accommodation unit (such as a loop) which constitutes the loop of an injector of a liquid chromatography apparatus (see reference numeral 40 in FIG. 3). In such an embodiment, it is possible, after each dilution stage, to perform an LC measurement of the sample after dilution up to the respective dilution stage. In other words, a representative of the dilution after each dilution stage may be measured by the further fluid accommodation unit and the liquid chromatography apparatus.

Figure 2:
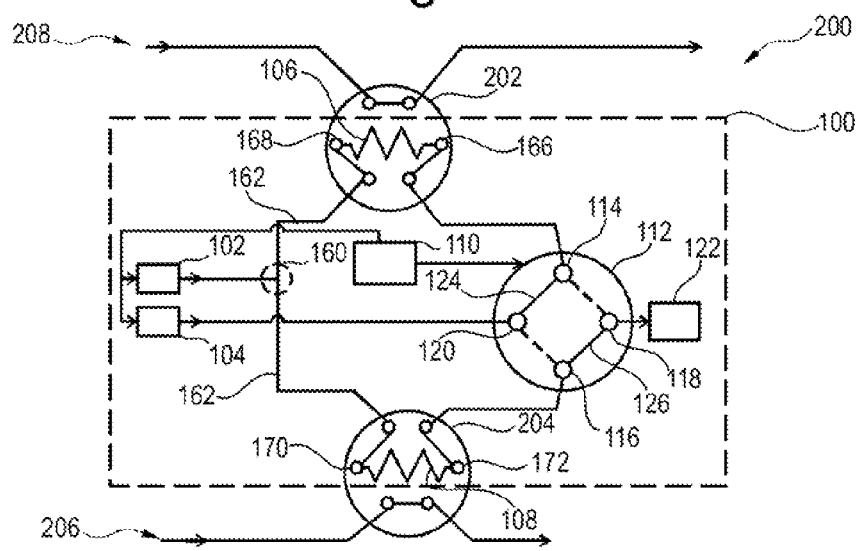
FIG. 2 shows the setup of a processing monitoring apparatus comprising a dilution apparatus as shown in FIG. 1 according to an exemplary embodiment of the invention.

FIG. 2 shows a beer brewing process monitoring apparatus 200 for monitoring a beer brewing process involving processing a processing fluid according to an exemplary embodiment of the invention.

As can be taken from FIG. 2, the process monitoring apparatus 200 comprises a beer brewing device 208 (only schematically shown in FIG. 2) along which a processing fluid (such as beer or a liquid required for brewing beer) flows and is made subject of a beer brewing process which is not described in detail here. A fluidic supply valve 202 is shown which may be constituted similar as the fluidic control valve 112 with the difference that, in the shown embodiment, the fluidic supply valve 202 is a six-port-three-groove valve, whereas the fluidic control valve 112 is a four-port-two-groove fluidic valve. In the shown operation mode, the fluidic supply valve 202 is in such a switching state that the processing fluid flows along the beer brewing processing device 208 without being disturbed by the remaining components of the processing monitoring apparatus 200. Hence, the beer brewing procedure takes presently place.

However, upon switching the fluidic supply valve 202 by 60, a sample of processing fluid is split or branched off from the beer brewing device 208 via the fluidic supply valve 202 into the dilution apparatus 100, more precisely is loaded onto the first fluid accommodation unit 106. Then, the dilution of the fluidic sample may be performed as described above referring to FIG. 1. At the end of this procedure, when the diluted fluidic sample is stored in the second fluid accommodation unit 108, a fluidic drain valve 204 may be switched so as to transfer the diluted fluidic sample from the second fluid accommodation unit 108 into a liquid chromatography analysis device 206. As can be taken from FIG. 2, the fluidic drain valve 204 is configured in a similar way as the fluidic supply valve 202. Hence, the second fluid accommodation unit 108 can, in the operation mode shown in FIG. 2, form part of the dilution apparatus 100. Upon switching the fluidic drain valve 204 for draining diluted fluidic sample, the second fluid accommodation unit 108 can be considered as part of the liquid chromatography device 206 and therefore the diluted fluidic sample may be injected into the liquid chromatography device 206.

In the liquid chromatography device 206, the diluted sample may be made subject of a liquid chromatography analysis so that it can be separated into its various fractions. A detector in the liquid chromatography device 206 can then detect the relative contributions of the fractions of the diluted fluidic sample. The detector output, which may be optionally processed or evaluated, may be used as a feedback parameter based on which operation of the beer processing in the beer processing device 208 can be adjusted. This may be for instance appropriate if the analysis in the liquid chromatography device 206 yields the result that there is a problem with any of the parameters of the beer brewing process.

FIG. 3 shows an example of a constitution of the liquid chromatography device 206, wherein the diluted fluidic sample can be injected, via the fluidic drain valve 204, onto an injector 40 and from there into the fluidic path between the fluid drive 20 and a chromatographic separation column 30. For instance, the second fluid accommodation unit 108 may form the sample loop of the injector 40. Particularly, the loop (i.e. the volume between interfaces 170 and 172) of the valve 204 can serve as the loop of the injector 40. This results in a compact design, as appreciated by those skilled in the art.

FIG. 3 depicts a general schematic of the liquid chromatography device 206. A pump 20 receives a mobile phase (also denoted as fluid) as a whole or as individual components that get mixed together by the pump 20. The pump 20—as a mobile phase drive—drives the mobile phase through a separating device 30 (such as a chromatographic column) comprising a stationary phase. Sampling device or injector 40 can be provided between the pump 20 and the separating device 30 in order to subject or add (often referred to as sample introduction) the diluted sample fluid (also denoted as diluted fluidic sample) into the mobile phase. The stationary phase of the separating device 30 is configured for separating compounds of the sample liquid.

A detector 50 is provided for detecting separated compounds of the sample fluid. A fractionating device 60 can be provided for collecting separated compounds of sample fluid.

A data processing device 70, which can be a conventional PC or workstation, might be coupled (as indicated by the dotted arrows) to one or more of the devices in the liquid chromatography device 206 in order to receive information and/or control operation. For example, the data processing device 70 might control operation of the pump 20 (for instance setting control parameters) and receive therefrom information regarding the actual working conditions (such as output pressure, quantity per time, etc.). The data processing device 70 might also control operation of the solvent supply (for instance setting the solvent/s or solvent mixture to be supplied). The data processing device 70 might further control operation of the sampling device 40 (for instance controlling sample injection or synchronization sample injection with operating conditions of the pump 20). The separating device 30 might also be controlled by the data processing device 70 (for instance selecting a specific flow path or column, setting operation temperature, etc.), and send—in return—information (for instance operating conditions) to the data processing device 70. Accordingly, the detector 50 might be controlled by the data processing device 70 (for instance with respect to spectral or wavelength settings, setting time constants, start/stop data acquisition), and send information (for instance about the detected sample compounds) to the data processing device 70. The data processing device 70 might also control operation of the fractionating device 60 (for instance in conjunction with data received from the detector 50) and provides data back.

Figure 4:
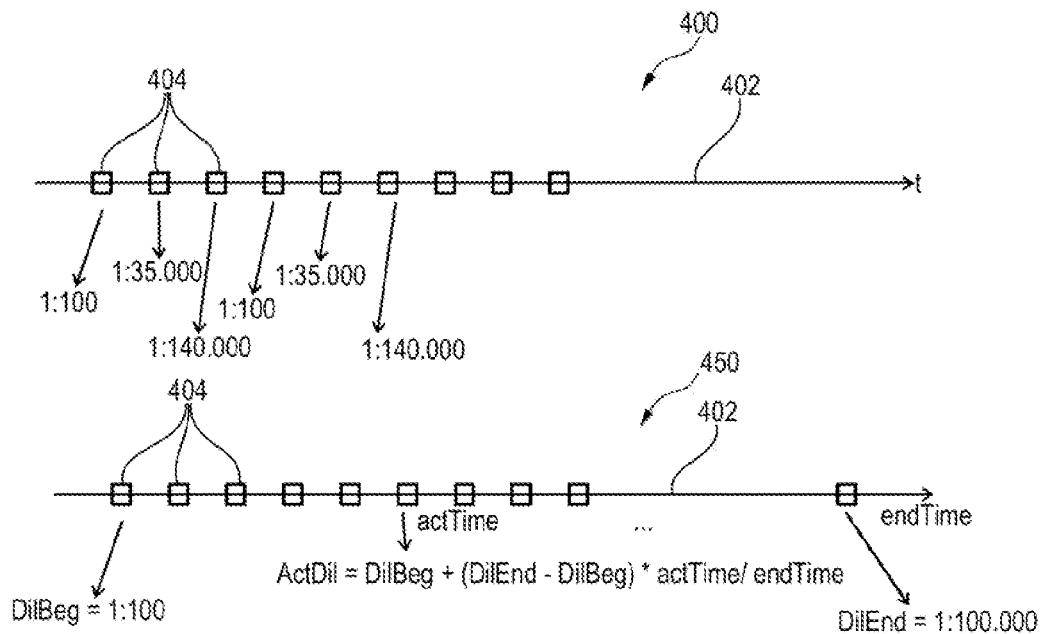
FIG. 4 shows examples for process monitoring involving a number of dilution experiments to be executed in accordance with a dilution sequence plotted along a time axes.

FIG. 4 schematically shows an example for a process monitoring process 400 involving a number of dilution experiments 404 to be executed in accordance with a dilution sequence plotted along a time axes 402. In the shown example, process monitoring is performed repetitively for three different compounds (first three dilution experiments 404, next three dilution experiments 404, last three dilution experiments 404) with three different dilution ratios (1:100, 1:35000, 1:140000) each.

FIG. 4 shows another example for a process monitoring process 450 involving a number of dilution experiments 404 to be executed in accordance with a dilution sequence plotted along a time axes 402. In the shown example, process monitoring is performed repetitively for linear interpolated dilutions ratios. A formula for calculating an actual dilution ratio ActDil at an actual time actTime from a dilution ratio at the beginning DilBeg is shown, so that an end dilution ratio DilEnd is obtained at an end time endTime.

Figure 5:
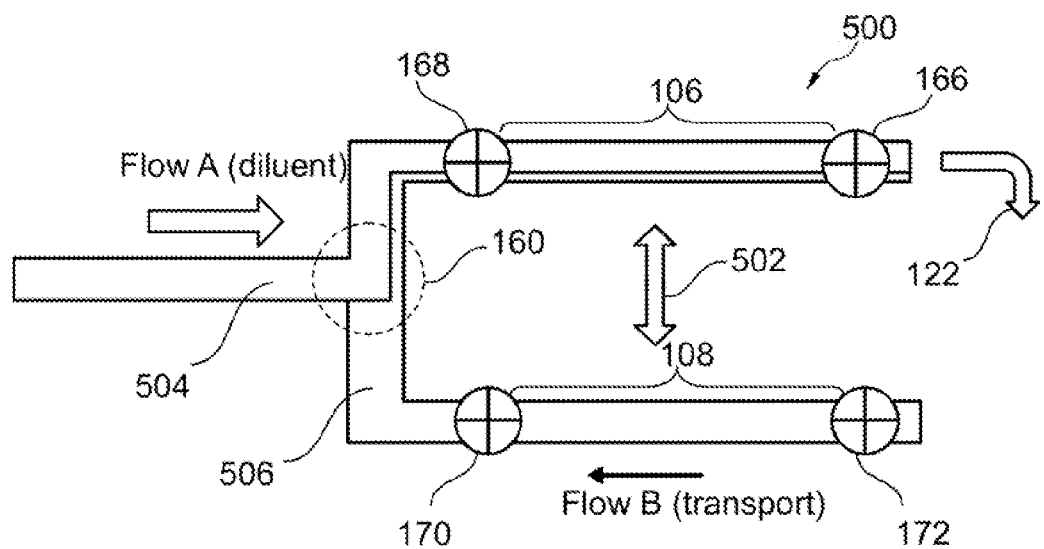
FIG. 5 shows a scheme illustrating the functioning principle of a dilution apparatus for diluting a fluidic sample according to an exemplary embodiment of the invention.

FIG. 5 shows a scheme 500 illustrating again the functioning principle of a dilution apparatus, such as the one shown in FIG. 1, for diluting a fluidic sample according to an exemplary embodiment of the invention.

In the shown scenario, a mixture 506 of dilution fluid 504 (or diluent, also denoted as Flow A) and fluidic sample is presently located at the second fluid accommodation unit 108. Transport fluid, also denoted as Flow B, is supplied to a back end of the mixture 506 to move this mixture 506 towards the flow combiner 160 or mixing point für initiating a next mixing stage. At the flow combiner 160, the mixture is mixed with further dilution fluid 504, and the resulting further diluted mixture is moved towards the first fluid accommodation unit 106. Before a next switch (indicated schematically by arrow 502) or reversal of the flowing direction of the further diluted mixture is performed, a part of the further diluted mixture is pumped towards waste 122 until the entire fluid volume of the first fluid accommodation unit 106, i.e. the full volume between fluidic interfaces 166 and 168, is completely filled with further diluted mixture in a defined and spatially constant concentration. In order to ensure a well-defined mixing ratio, it is advantageous to ensure that, at the time of switching, always the whole fluid accommodation unit is filled with diluted sample at well-defined conditions and that undefined fluid sections preceding or succeeding such a well-defined fluid packet are cut-off and are not loaded onto a fluid accommodation unit directly prior to a subsequent switch of the operation mode.

It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

The invention claimed is:

1. A dilution apparatus for diluting a fluidic sample, in accordance with a specifiable dilution ratio, the dilution apparatus comprising:
   a dilution fluid supply device configured for supplying a dilution fluid, at a first quantity per time being flow rate A;
   a transport fluid supply device configured for supplying a transport fluid, at a second quantity per time being flow rate B;
   a first fluid accommodation unit configured for accommodating a first fluid volume;
   a second fluid accommodation unit configured for accommodating a second fluid volume;
   a control device configured for controlling flow of the dilution fluid, the transport fluid and the fluidic sample so that:
   in a first operation mode, the fluidic sample, being accommodated in the first fluid accommodation unit, is forced to flow to the second fluid accommodation unit at the flow rate B of the transport fluid while the fluidic sample is diluted by being mixed with the dilution fluid at a flow rate A;
   in a second operation mode, the mixture of the dilution fluid and the fluidic sample, being accommodated in the second fluid accommodation unit, is forced to flow from the second fluid accommodation unit to the first fluid accommodation unit while being further diluted by being mixed with further dilution fluid such that the specifiable dilution ratio is based at least on flowrates of the dilution fluid compared to flowrates of the transport fluid.

2. The dilution apparatus according to claim 1, wherein the control device is configured for adjusting a quantity per time of supplying the dilution fluid and/or a quantity per time of supplying the transport fluid to thereby adjust the dilution ratio to a user-defined or a predefined dilution ratio.

3. The dilution apparatus according to claim 1, wherein the control device is configured for opening the dilution apparatus alternatingly in the first operation mode and subsequently in the second operation mode for a specifiable number of times to thereby adjust the dilution ratio to the specifiable dilution ratio.

4. The dilution apparatus according to claim 1, wherein the dilution fluid supply device and the transport fluid supply device are configured for supplying the same kind of fluid, as a dilution fluid and as a transport fluid.

5. The dilution apparatus according to claim 1, wherein the control device comprises a fluidic control valve being switchable to operate the dilution apparatus alternatingly in the first operation mode and in the second operation mode.

6. The dilution apparatus according to claim 5, wherein the control device is configured for switching the fluidic control valve to move the fluidic sample alternatingly along a first direction, in a counterclockwise or in a clockwise direction, in the first operation mode and along a second direction, in a clockwise or in a counterclockwise direction, in the second operation mode, the second direction being opposite to the first direction.

7. The dilution apparatus according to claim 5, wherein the fluidic control valve comprises a first valve member, comprising a stator, comprising ports and a second valve member, comprising a rotor, comprising grooves configured for fluidically coupling selectable ones of the ports depending on a relative orientation between the first valve member and the second valve member which are movable relative to one another.

8. The dilution apparatus according to claim 7,
wherein a first port is fluidically coupled to the first fluid accommodation unit, a second port is fluidically coupled to the second fluid accommodation unit, a third port is fluidically coupled to the transport fluid supply device, and a fourth port is fluidically coupled to a waste line; wherein the dilution fluid supply device is fluidically connected between the first fluid accommodation unit and the second fluid accommodation unit;
wherein the fluidic control valve is switchable so that:
in the first operation mode, one groove connects the first port to the third port and another groove connects the second port with the fourth port;
in the second operation mode, one of the grooves connects the first port to the fourth port and the other one of the grooves connects the second port with the third port.

9. The dilution apparatus according to claim 1, wherein the control device is configured for, prior to each switch between the first operation mode and the second operation mode, draining a portion of the mixture towards a waste line until the entire fluid volume of the respective one of the fluid accommodation units is completely filled with the mixture before further diluting the remaining portion of the mixture after a subsequent change of the operation mode.

10. The dilution apparatus according to claim 1, wherein the transport fluid supply device is configured, in each of the first and the second operation mode, for pressing the transport fluid towards a respective back end of the fluidic sample or the mixture to thereby drive the fluidic sample or the mixture to a position at which subsequent mixing or further mixing with dilution fluid occurs.

11. The dilution apparatus according to claim 1, wherein the transport fluid supply device is configured, in each of the first and the second operation mode, for pressing the transport fluid towards a respective back end of the fluidic sample or the mixture without mixing the fluidic sample or the mixture with transport fluid.

12. The dilution apparatus according to claim 1, comprising a mixing point, comprising a flow combiner, fluidically connecting a flow path from the first fluid accommodation unit with a flow path from the second fluid accommodation unit and with a flow path from the dilution fluid supply device to enable mixing between the fluidic sample or the mixture with dilution fluid at the mixing point.

13. The dilution apparatus according to claim 12, wherein the mixing point is selected from the group consisting of an active mixer and a passive mixer.

14. A process monitoring apparatus for monitoring a process of processing a processing fluid, the process monitoring apparatus comprising:
a fluidic sample supply device configured for supplying a fluidic sample of the processing fluid;
a dilution apparatus according to claim 1 configured for being supplied with the fluidic sample and for diluting the supplied fluidic sample, in accordance with a specifiable dilution ratio;
a diluted fluidic sample drain device configured for draining diluted fluidic sample;
an analysis device configured for analyzing the drained diluted fluidic sample for monitoring the process.

15. The process monitoring apparatus according to claim 14, wherein the analysis device comprises a sample separation device configured for separating different fractions of the diluted fluidic sample.

16. The process monitoring apparatus according to claim 15, wherein the sample separation device is a liquid chromatography device configured for separating the different fractions of the diluted fluidic sample by liquid chromatography.

17. The process monitoring apparatus according to claim 16, wherein the liquid chromatography device comprises:
a fluid drive configured to drive a mobile phase and the diluted fluidic sample along a separation path;
a chromatographic column located in the separation path downstream of the fluid drive and being configured for separating the fractions of the diluted fluidic sample fluid in the mobile phase.

18. The process monitoring apparatus according to claim 17, comprising at least one of the following features:
the liquid chromatography device comprises a sample injector configured to receive the diluted fluidic sample from the diluted fluidic sample drain device and to introduce the diluted fluidic sample into the mobile phase;
the liquid chromatography device comprises a degassing apparatus for degassing the mobile phase.

19. The process monitoring apparatus according to claim 14, comprising at least one of the following features:
wherein the fluidic sample is one of the group consisting of a biological sample, a pharmaceutical sample, a chemical sample, and a food sample;
the analysis device comprises a detector configured to detect separated fractions of the diluted fluidic sample;
the analysis device comprises a collection device configured to collect separated fractions of the diluted fluidic sample;

the analysis device is configured to analyze at least one physical, chemical and/or biological parameter of at least one compound of the diluted fluidic sample;

the analysis device comprises at least one of the group consisting of a chromatography device, a liquid chromatography device, an HPLC device, a gas chromatography device, a capillary electrochromatography device, an electrophoresis device, a capillary electrophoresis device, a gel electrophoresis device, and a mass spectroscopy device.

20. The process monitoring apparatus according to claim 14, comprising a fluid processing device configured for processing the processing fluid, wherein the fluidic sample supply device is configured for supplying the fluidic sample to the first fluid accommodation unit.

21. The process monitoring apparatus according to claim 20, wherein the fluid processing device comprises at least one of the group consisting of a product manufacturing device, a pharmaceutical process device, and an experimental process device.

22. The process monitoring apparatus according to claim 20, wherein the fluidic sample supply device comprises a fluidic supply valve being switchable so as to transfer fluidic sample of the fluid processing device to the first fluid accommodation unit.

23. The process monitoring apparatus according to claim 14, wherein the diluted fluidic sample drain device comprises a fluidic drain valve being switchable so as to transfer diluted fluidic sample from the second fluid accommodation unit to the analysis device.

24. A method of diluting a fluidic sample, in accordance with a specifiable dilution ratio, the method comprising
supplying a dilution fluid, at a first quantity per time at a flow rate A;
supplying a transport fluid at a second quantity per time at a flow rate B;
supplying the fluidic sample, a predefined amount of fluidic sample;
controlling flow of the dilution fluid, the transport fluid and the fluidic sample so that:
in a first operation mode, the fluidic sample, being accommodated in a first fluid accommodation unit configured for accommodating a first fluid volume, is forced to flow by the transport fluid at the flow rate B to a second fluid accommodation unit, the second fluid accommodation unit configured for accommodating a second fluid volume while being diluted by being mixed with dilution fluid;
in a second operation mode, the mixture of the dilution fluid and the fluidic sample, being accommodated in the second fluid accommodation unit, is forced to flow from the second fluid accommodation unit to the first fluid accommodation unit while being further diluted by being mixed with further dilution fluid such that the specifiable dilution ratio is based at least on flowrates of the dilution fluid compared to flowrates of the transport fluid.

25. A non-transitory computer readable software program or product, stored on a data carrier, for executing a method according to claim 24, when run on a data processing system.

26. A dilution apparatus for dilution of a fluidic sample in accordance with a specifiable dilution ratio, the dilution apparatus comprising:
a first accommodation volume configured for accommodating a first fluid;
a second accommodation volume configured for accommodating a second fluid;
a dilution fluid supply device configured for supplying a dilution fluid at a defined quantity per time being a dilution flow rate;
a transport fluid supply device configured for supplying a transport fluid at a defined quantity per time being a transport flow rate;
a mixing point in fluidic communication with the first accommodation volume, the second accommodation volume, and the dilution fluid supply device;
a control device being configured for initially introducing the fluidic sample into the first accommodation volume and for switching between operation modes, the control device further being configured for:
a) in a first operation mode, simultaneously moving the fluid from the first accommodation volume driven by the transport fluid of the transport fluid supply device and the dilution fluid driven by the dilution fluid supply device through the mixing point and into the second accommodation volume to fill the second accommodation volume with the diluted mixture, and
b) in a second operation mode, simultaneously moving the fluid from the second accommodation volume driven by the transport fluid of the transport fluid supply device and the dilution fluid driven by the dilution fluid supply device through the mixing point and into the first accommodation volume to fill the first accommodation volume with the diluted mixture;
wherein the dilution ratio is determined by a respective ratio of the transport flow rate and the dilution flow rate in a respective operation mode as well as by a number of times switched between the operation modes.

27. The dilution apparatus of claim 26, wherein
in the first operation mode, the fluid from the first accommodation volume is driven by the transport fluid of the transport fluid supply device and the dilution fluid driven by the dilution fluid supply device through the mixing point and into the second accommodation volume to completely fill the second accommodation volume with the diluted mixture in a defined and spatially constant concentration, and
in the second operation mode, the fluid from the second accommodation volume is driven by the transport fluid of the transport fluid supply device and the dilution fluid driven by the dilution fluid supply device through the mixing point and into the first accommodation volume to completely fill the first accommodation volume with the diluted mixture in a defined and spatially constant concentration.

* * * * *